US010030212B2

(12) United States Patent
Xiang et al.

(10) Patent No.: US 10,030,212 B2
(45) Date of Patent: Jul. 24, 2018

(54) METHOD FOR PREPARING GLYCERIDE TYPE POLYUNSATURATED FATTY ACIDS

(71) Applicant: Zhejiang Medicine Co., Ltd. Xinchang Pharmaceutical Factory, Zhejiang (CN)

(72) Inventors: Xuebing Xiang, Zhejiang (CN); Xinde Xu, Zhejiang (CN); Bin Shao, Zhejiang (CN); Chong Li, Zhejiang (CN)

(73) Assignee: ZHEJIANG MEDICINE CO., LTD. XINCHANG PHARMACEUTICAL FACTORY, Xinchang County, Zhejiang Province (CN)

( * ) Notice: Subject to any disclaimer, the term of this patent is extended or adjusted under 35 U.S.C. 154(b) by 0 days.

(21) Appl. No.: 15/519,015

(22) PCT Filed: Oct. 12, 2015

(86) PCT No.: PCT/CN2015/000687
§ 371 (c)(1),
(2) Date: Apr. 13, 2017

(87) PCT Pub. No.: WO2016/058284
PCT Pub. Date: Apr. 21, 2016

(65) Prior Publication Data
US 2017/0226446 A1    Aug. 10, 2017

(30) Foreign Application Priority Data

Oct. 13, 2014  (CN) .......................... 2014 1 0538808

(51) Int. Cl.
*C11C 3/06* (2006.01)
(52) U.S. Cl.
CPC ..................... *C11C 3/06* (2013.01)
(58) Field of Classification Search
CPC ................... C11C 3/06; C07C 67/02
See application file for complete search history.

(56) References Cited

U.S. PATENT DOCUMENTS

| 5,149,851 | A  | * | 9/1992 | Stout ........................ C11C 3/06 554/165 |
| 6,395,778 | B1 | * | 5/2002 | Luthria .................... C11B 1/025 514/549 |
| 7,179,929 | B2 | * | 2/2007 | Horlacher ............... C07C 67/03 554/124 |
| 2009/0023808 | A1 | * | 1/2009 | Raman ..................... A21D 2/16 514/549 |

FOREIGN PATENT DOCUMENTS

| CN | 1132195    | 10/1996 |
| CN | 1447850    | 10/2003 |
| CN | 1884564    | 12/2006 |
| CN | 101161819  | 4/2008  |
| CN | 101255380  | 9/2008  |
| CN | 101796014  | 8/2010  |
| CN | 101818176  | 9/2010  |
| CN | 102028711  | 4/2011  |
| CN | 102277237  | 12/2011 |
| CN | 102959083  | 3/2013  |
| CN | 102964249  | 3/2013  |
| CN | 103242969  | 8/2013  |
| CN | 101736044  | 10/2013 |
| CN | 103436563  | 12/2013 |
| JP | 2000213359 | 8/2000  |

OTHER PUBLICATIONS

CN 103242969, Kinomega Biopharm Inc., Preparation method of triglyceride type fish oil and prepared triglyceride type fish oil, Aug. 4, 2013, pp. 1-8 (English translation).*
International Search Report and Written Opinion (English and Chinese) of international application No. PCT/CN2015/000687, dated Jan. 18, 2016. (14 pages).

* cited by examiner

*Primary Examiner* — Yate Kai Rene Cutliff
(74) *Attorney, Agent, or Firm* — Hamre, Schumann, Mueller & Larson, P.C.

(57) ABSTRACT

The present invention relates to a method for preparing glyceride type polyunsaturated fatty acids. The method comprises: firstly mixing a basic catalyst with glycerol or a glyceride uniformly; then adding the mixture to a polyunsaturated fatty acid material slowly, and carrying out an esterification reaction under certain conditions to obtain glyceride type polyunsaturated fatty acids, wherein the basic catalyst is a lower aliphatic alcohol sodium/potassium or a solution thereof. The procedure of the process is simple, has mild reaction conditions, short reaction time, high yield and good quality of the obtained product.

9 Claims, No Drawings

METHOD FOR PREPARING GLYCERIDE TYPE POLYUNSATURATED FATTY ACIDS

FIELD OF THE INVENTION

The present invention relates to a method for preparing glyceride type polyunsaturated fatty acids by performing a esterification of polyunsaturated fatty acid material with glycerol or glyceride under a basic catalyst to obtain a glyceride type polyunsaturated fatty acid. The method creatively uses a lower aliphatic alcohol sodium or potassium or its solution as a catalyst. The method greatly improves esterification degree, reduces reaction time, improves reaction yield, and moreover minimizes the destruction on the polyunsaturated fatty acid material due to strong basic catalyst, to obtain higher quality of the glyceride type polyunsaturated fatty acid.

BACKGROUND OF THE INVENTION

With the progress of society and abundance of people lives, the public pays more and more attention to their health. The public is interested in scientific research and nutritional supplement of polyunsaturated fatty acids (PUFA) such as fish oil.

PUFA is an important basic substance for body metabolism, especially for infant brain development. PUFA is a component of cell membrane, and plays a role on physiological functions such as maintaining cell membrane fluidity, reducing cholesterol, improving insulin sensitivity, decreasing blood glucose, decreasing cholesteremia, and reducing fat accumulation, treatment of diabetes, lowering blood pressure, regulating heart rate, regulating thrombosis and treatment of arthritis. However, PUFA cannot be synthesized by the body itself. PUFA must be obtained from diet.

There are various kinds of PUFA including ω-3 PUFA, ω-6 PUFA, ω-9 PUFA, and other kinds of conjugated linoleic acid, such as α-Linolenic acid (ALA), eicosapentaenoic ester (EPA), docosahexaenoic acid (DHA), docosapentaenoic acid (DPA), linoleic acid (LA), conjugated linoleic acid (CLA), γ-linolenic acid (GLA), arachidonic acid (AA) and so on. Wherein EPA and DHA representing ω-3 PUFA are known and acceptable to the public. and obviously improve human thinking and enhance memory. Their molecular structures of polyunsaturated fatty acids are as follows.

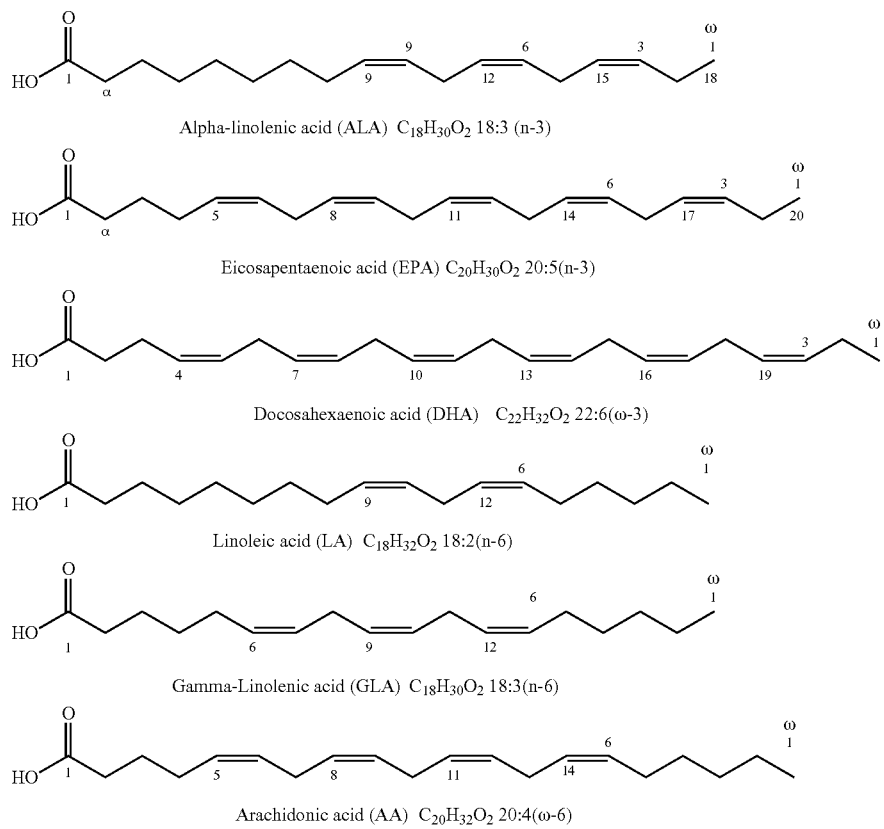

Alpha-linolenic acid (ALA) $C_{18}H_{30}O_2$ 18:3 (n-3)

Eicosapentaenoic acid (EPA) $C_{20}H_{30}O_2$ 20:5(n-3)

Docosahexaenoic acid (DHA) $C_{22}H_{32}O_2$ 22:6(ω-3)

Linoleic acid (LA) $C_{18}H_{32}O_2$ 18:2(n-6)

Gamma-Linolenic acid (GLA) $C_{18}H_{30}O_2$ 18:3(n-6)

Arachidonic acid (AA) $C_{20}H_{32}O_2$ 20:4(ω-6)

Polyunsaturated fatty acids mainly derive from algae extract and marine oil. One of important sources comes from fish oil.

At present, glyceride type polyunsaturated fatty acids occupy a large proportion in main application forms of polyunsaturated fatty acid products or materials in industry, because glyceride type polyunsaturated fatty acids are more stable relative to free type polyunsaturated fatty acids and ethyl ester type polyunsaturated fatty acids. Free type polyunsaturated fatty acids are easily oxidized, and their bioavailability of ethyl ester type polyunsaturated fatty acids and methyl ester type polyunsaturated fatty acids in the body is lower and consequently there would be some safety problems. Moreover the bioavailability of the glyceride type polyunsaturated fatty acid in the body is higher than other types of polyunsaturated fatty acids, and the glyceride type polyunsaturated fatty acids have also been proved to have better security.

It would be very difficult to obtain glyceride type polyunsaturated fatty acids by direct distillation or other methods because of higher boiling point of glyceride type polyunsaturated fatty acids. At present, glyceride type polyunsaturated fatty acids in industry are mainly obtained by a direct esterification or transesterification of polyunsaturated fatty acids such as free-type or ethyl ester-type or methyl ester-type with glycerol or glyceride.

The prior art mainly includes that a polyunsaturated fatty acid material performs a esterification or transesterification with glycerol or glyceride by adding lipase catalyst or adding sodium hydroxide or potassium hydroxide and other alkali catalyst or adding zinc powder for protection without catalyst at high temperature, and then obtains glyceride type polyunsaturated fatty acid products after subsequent processing. Difficulties of the process mainly focus on poor reaction activity of glycerides, and raw materials or products are easily oxidized and destroyed because of many double bonds in their molecular structures.

The lipase catalytic process has the following drawbacks: 1) the reaction cost is higher because of higher cost of enzyme; 2) the final product has some limitation because of selectivity of enzyme catalysis, for example, an enzyme catalysis is effective for 1,3-position hydroxyl of glycerol but invalid for 2-position hydroxyl of glycerol; 3) the lipase catalytic process has a longer reaction time generally and consequently results in certain difficulties in large scale industrial production; 4) enzymes in the reaction are easily affected by raw materials or environmental factors and consequently results in inactivation of enzymes. The prior process has higher demand for raw materials and environment, and the cost of enzyme catalytic process is also higher. So the prior process has certain limitation in large-scale production in industry.

The chemical catalytic process of preparing glyceride type polyunsaturated fatty acids by adding sodium hydroxide or potassium hydroxide and other strong alkaline catalyst also has some deficiencies as follows: 1) sodium hydroxide or potassium hydroxide or other strong alkaline has certain destructive effects on raw materials of polyunsaturated fatty acids; 2) the prior art has larger amount of catalyst, higher reaction temperature, less complete reaction, lower reaction yield and longer reaction time, because of poorer catalytic activity of sodium hydroxide or potassium hydroxide. So it would lead to certain destructive effects on raw materials of polyunsaturated fatty acids, darker product color. So the final product quality is poor.

Non-catalytic process of preparing glyceride type polyunsaturated fatty acids is mainly limited to necessarily use free type polyunsaturated fatty acids as raw materials. It is necessary to hydrolyze a variety of ester types of polyunsaturated fatty acids to obtain free type polyunsaturated fatty acids firstly, and then perform esterification or transesterification. So the process is more complicated. At the same time, the prior process has low reaction degree, low reaction yield, longer reaction time, higher reaction temperature, because of no catalyst in the reaction. So the final product quality is poor.

At present, some literatures disclose processes of preparing glyceride type polyunsaturated fatty acid by adding polyunsaturated fatty acid materials.

Patent CN102277237 mainly describes to perform a saponification of ethyl ester-type polyunsaturated fatty acids, and then acidify and wash, and recycle solvent to obtain free-type polyunsaturated fatty acids, and then add zinc powder, sodium hydroxide or potassium hydroxide as catalyst to free type polyunsaturated fatty acids to react together at 180~225° C., finally go through a quenching reaction by rapid cooling, and then extract, wash, drying and concentrate in turn, to obtain glyceride type polyunsaturated fatty acids. The process is more complicated, poor product quality, 80% of product yield.

Patent CN103242969 describes to directly react ethyl ester-type polyunsaturated fatty acids with glycerol to obtain glyceride type polyunsaturated fatty acids by adding sodium hydroxide or potassium hydroxide as catalyst. The process needs high reaction temperature due to poor catalytic activity of the catalyst. So the product quality is poor, and the reaction yield is also low about 70%.

Patents JP200213359, CN101161819, CN101255380, CN10176044, CN1884564, CN101818176, CN103436563, CN102028711 describes a process of reacting ester type polyunsaturated fatty acids or free type polyunsaturated fatty acids with glycerol or glyceride by adding lipase catalyst to prepare glyceride polyunsaturated fatty acids. The process has some deficiencies such as higher cost of lipase, selective position of glycerol esterification, poisonous lipase, complicated process, higher cost.

In general, the prior processes of glyceride type polyunsaturated fatty acids have one or more deficiencies such as 1) complicated process and higher cost; 2) low reaction degree and longer reaction time and lower yield; 3) easily damaged of raw materials and poor product quality due to high temperature or strong acidity or basicity.

In general, glyceride type polyunsaturated fatty acid products are mainly obtained by reacting polyunsaturated fatty acid materials with glycerol or glyceride. But it would result in difficulty of direct reaction with polyunsaturated fatty acid materials because glycerol or glyceride with three reaction sites has structural steric hindrance and low reactivity of glycerol or glyceride. Besides, strong acids as necessary catalyst would directly cause destruction of raw materials, but weak acids or weak bases as catalyst could not catalyze such a reaction because of poor catalyst activity of weak acids or weak bases.

Strong basic catalysts have relatively better catalytic activity for such a reaction, and consequently are widely used in preparation of lower fatty acid esters. Such a process has good effects, small destruction on raw materials and better product quality. However, as for the preparation of higher fatty acid esters, the alkalinity of catalysts could have a certain degree of damage on raw materials especially lower stable raw materials. Wherein, the activity of sodium hydroxide or potassium hydroxide is poor. So it would need a big feeding amount of catalyst. But it would result in incomplete reaction and low yield in the process of preparing polyunsaturated fatty acid. And the alkalinity of catalysts has more serious effects on polyunsaturated fatty acid materials and produces poor quality products. The alkalinity of sodium or potassium alkoxides or its solutions as catalyst would have destructive to raw materials and products and obtain poor quality products, although sodium or potassium alkoxides or its solutions with smaller amount have better catalytic activity.

SUMMARY OF THE INVENTION

The present invention relates to a method for preparing glyceride type polyunsaturated fatty acids by performing a esterification of polyunsaturated fatty acid material with glycerol or glyceride under a basic catalyst to obtain a glyceride type polyunsaturated fatty acid. The method comprises: firstly mixing a basic catalyst with glycerol or a glyceride uniformly to form a mixture; then adding the mixture to a polyunsaturated fatty acid material slowly, and carrying out an esterification reaction under certain conditions to obtain glyceride type polyunsaturated fatty acids, wherein the basic catalyst is a lower aliphatic alcohol sodium or potassium or a solution thereof. The procedure of the process is simple, has mild reaction conditions, short reaction time, high yield and good quality of the obtained product.

In particular, the method of the present invention includes the following steps:

1) feeding: firstly mixing a basic catalyst with glycerol or glyceride uniformly to obtain a mixture, then adding the mixture to a polyunsaturated fatty acid material slowly under stirring;

2) reaction: heating to 80~200° C. of temperature after completion of feeding, and then recovering low boiling point substances produced by the reaction by condensating; and 3) washing and recycling product: cooling the reaction vessel to 0~60° C., after completion of the reaction, adding a small amount of water to extract a basic catalyst, and recovering a small amount of remaining water in an organic layer, to obtain a glyceride type polyunsaturated fatty acid product.

The process of the present invention is overall simple, has mild reaction conditions, easily obtained catalysts, low costs, high yield and good quality of the obtained product.

The procedure of the process is as follows:

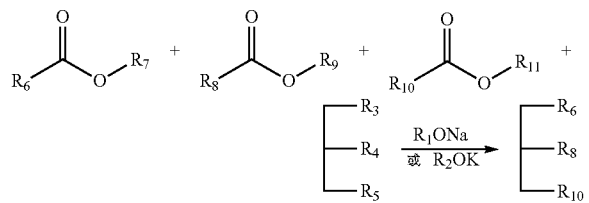

Wherein R1, R2 represent $C_1$~$C_5$ alkyl group; $R_3$, $R_4$, $R_5$ represent same or different hydroxyl group or $C_1$~$C_4$ lower carboxylic acid group; $R_6$, $R_8$, $R_{10}$ represent same or different hydroxyl group or $C_1$~$C_4$ lower carboxylic acid group or $C_6$~$C_{40}$ alkenyl group; $R_6$, $R_7$ and $R_8$ cannot be simultaneously hydroxyl group or simultaneously $C_1$~$C_4$ lower carboxylic acid group; $R_7$, $R_9$, $R_{11}$ are same or different H or $C_1$~$C_4$ alkyl group;

In comparison with other prior processes, the present invention has many advantages as follows: 1) simple process, low cost; 2) high reaction degree, short reaction time, and high yield; 3) mild reaction conditions, less destruction to raw materials and products, and better quality of the obtained products; 4) simple and easy operation, large-scale production to be easy implement; 5) without destruction and pollution on environment; 6) better process safety.

The process of the present invention creatively uses a lower aliphatic alcohol sodium or potassium or its solution as a catalyst and furthest overcome deficiencies of destruction of lower aliphatic alcohol sodium or potassium on raw materials and products by selection and optimization of process conditions, to obtain glyceride type polyunsaturated fatty acid products with high quality.

Lower fatty acid sodium or potassium or its solution as catalyst in the process has such advantages as strong catalytic activity, less amount catalyst, higher reaction degree, shorter reaction time and lower reaction temperature. At the same time, the process of the process is overall relatively mild by selection and optimization of process conditions. The finally glyceride type polyunsaturated fatty acid product has higher yield and better quality.

The lower aliphatic alcohol sodium or potassium or its solution comprises one or more of sodium alcoholate with formula R1-ONa, a solution of sodium alcoholate with formula R1-ONa, potassium alcoholate with formula $R_2$—OK and a solution of potassium alcoholate with formula $R_2$—OK. Wherein $R_1$, $R_2$ represent lower alkyl group having $C_1$~$C_5$ such as methyl, ethyl, propyl, isopropyl, butyl, isobutyl, tert-butyl, pentyl, isopentyl, tert-pentyl.

The process condition of the present invention comprises the weight ratio of three substances comprising the polyunsaturated fatty acid material, glycerol or glyceride and the basic catalyst is 100:1~100:0.1~10; the reaction temperature is 80~200° C., the reaction time is 1~10 hours.

The term "polyunsaturated fatty acid materials" described in the present invention is referred to as the polyunsaturated fatty acid with formula

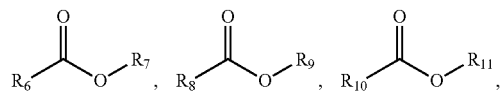

wherein $R_6$, $R_8$, $R_{10}$ are same or different $C_6$~$C_{40}$ alkenyl group; $R_7$, $R_9$, $R_{11}$ are same or different H or $C_1$~$C_4$ alkyl group such as one or more polyunsaturated fatty acids of free-type polysaturated fatty acids, methyl ester-type polyunsaturated fatty acids, ethyl ester-type polyunsaturated fatty acids.

The term "polyunsaturated fatty acid materials" described in the present invention is referred to as one or more polyunsaturated fatty acids comprising fish oil (ω-3 polyunsaturated fatty acid extracted directly), algae oil (ω-3 polyunsaturated fatty acid from fermentation), linoleic acid, conjugated linoleic acid, linolenic acid and arachidonic acid with various of contents, wherein the total content of the polyunsaturated fatty acid is 10~100 wt %

The term "glycerol or glyceride" comprises glycerol materials with formula

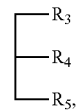

wherein $R_3$, $R_4$, $R_5$ represent same or different hydroxyl group or $C_1$~$C_4$ lower carboxylic acid group, such as formic acid group, acetic acid group, propionic acid group, n-butyric acid group, isobutyric acid group.

The process of the present invention selects lower aliphatic alcohol sodium or potassium or its solution as reaction catalysts. It could minimize amount of strong alkaline catalysts and reduce reaction temperatures and make process conditions milder. And slowly adding glycerol and diluent basic catalyst reduces destruction of strong basic catalysts on raw materials and polyunsaturated fatty acid material products. Besides selecting the best process conditions improves reaction degree and shortens the reaction time, and finally obtains high quality of the glyceride type polyunsaturated fatty acid product.

The process of the present invention has such advantages as less catalyst, simple catalyst, low cost, simple equipment and simple process. The reaction is carried out by one step reaction by direct conversion of the polyunsaturated fatty acid material to glyceride type polyunsaturated fatty acid with better quality product. The process of the present invention has the advantages of good safety and environmental protection and is suitable for large-scale industrial production.

DETAILED DESCRIPTION AND PREFERRED EMBODIMENTS THEREOF

Hereafter, the present invention will be described specifically with reference to the examples. The examples are given only for illustration of the technical solution of the present invention and should not be construed to limit the present invention.

Example 1

50 g of glycerol and 1.0 g of sodium methoxide are mixed together, then 500 g of ethyl ester type fish oil material (EPA 22.1%, DHA 14.3%, the total content of the ethyl ester type polyunsaturated fatty acid is 59.8%) is added into a reaction flask to form a mixture. The mixture of glycerol and sodium methoxide is slowly added to the reaction flask under stirring, and then heating, and an esterification is carried out at 80° C. for 1.0 hour.

The reaction flask is cooled to 50° C., and adding 20 ml of water, stirring uniformly, and then standing for 10 minutes for layering. The upper organic layer is undergone under atmospheric pressure or reduced pressure to recycle a small amount of water, to obtain 496 g of a glyceride type polyunsaturated fatty acid product. The lower wastewater is acidated by adding dilute sulfuric acid to recycle a small amount of organic matter to get wastewater, and the wastewater reaches a discharge standard for directly discharge.

It may be seen by testing the glyceride type fish oil product that the product has 21.9% of EPA, 14.2% of DHA, and the total content of glyceride type polyunsaturated fatty acid is 60.12%, wherein the triglyceride polyunsaturated fatty acid is 95.5% of the glyceride type polyunsaturated fatty acid, and the total content of the ethyl ester polyunsaturated fatty acid is 0.07%, with 97.9% of yield, and good quality of the product.

Comparative Example 2

50 g of glycerol and 5.0 g of sodium hydroxide are mixed together to form a mixture, and then 500 g of ethyl ester type fish oil material (EPA 22.1%, DHA 14.3%, the total content of the ethyl ester type polyunsaturated fatty acid is 59.8%) is added into a reaction flask. The mixture of glycerol and sodium hydroxide is slowly added to the reaction flask under stirring, and then heating, and then an esterification is carried out at 160° C. for 1.0 hour.

The reaction flask is cooled to 50° C., and adding 20 ml of water, stirring uniformly, and then standing for 10 minutes for layering. The upper organic layer is undergone under atmospheric pressure or reduced pressure to recycle a small amount of water, to obtain 472 g of a glyceride type polyunsaturated fatty acid product. The lower wastewater is acidated by adding dilute sulfuric acid to recycle a small amount of organic matter to get wastewater, and the wastewater reaches a discharge standard for directly discharge.

It may be seen by the testing glyceride type fish oil product that the product has 13.4% of EPA, 8.1% of DHA, and the total content of glyceride type polyunsaturated fatty acid is 20.12%, wherein the triglyceride polyunsaturated fatty acid is 36.2% of the glyceride type polyunsaturated fatty acid, and the total content of the ethyl ester polyunsaturated fatty acid is 15.72%, with 34.9% of yield, and the reaction is incomplete, with low yield and poor quality of the products.

It can be seen from Example 1 of the present invention that the process of the present invention obtains the glyceride type polyunsaturated fatty acid product by adding sodium methoxide as catalyst at milder reaction condition such as a lower temperature. The process is overall simple and easy to operate, has very high reaction degree, higher yield and better quality of product.

The comparative example 2 selects 160° C. as a temperature condition to obtain a glyceride type fish oil product by conventional esterification process of sodium hydroxide. But the process cannot be carried out at a low temperature condition. The reaction degree is lower because the activity of sodium hydroxide is lower. The content of glyceride type fish oil product is significantly reduced because parts of raw materials and products are destroyed. So the yield is very low, and the product quality is poor.

The process of the present invention selects lower aliphatic alcohol sodium or potassium or its solution as reaction catalysts. It could minimize amount of strong alkaline catalyst and reduce reaction temperatures to make process conditions milder. And slowly adding glycerol and diluent basic catalyst reduces destruction of strong basic catalysts on raw materials and the polyunsaturated fatty acid material. Besides selecting better process conditions improves reaction degree and shortens the reaction time, and finally obtains high quality of the glyceride type polyunsaturated fatty acid product.

The process of the present invention has such advantages as less catalyst, simple catalyst, low cost, simple equipment and simple process. The process is carried out by one step by one step, that is, a polyunsaturated fatty acid material is converted into a glyceride type polyunsaturated fatty acid with better quality product. The process of the present invention has good safety and environmental protection and is suitable for large-scale industrial production.

Examples 3-15

The objects of related parameters of Examples 3~10 are listed in the following Table.

| Example | Polyunsaturated fatty acid material | Total content of polyunsaturated fatty acid (%) | Glycerol or Glyceride (g/g) | Catalyst (g/g) | Temperature (° C.) | Reaction time (Hr) | Content of glyceride type polyunsaturated fatty acid (%) | Relative content of triglyceride polyunsaturated fatty acid (%) | Yield (%) |
|---|---|---|---|---|---|---|---|---|---|
| 3 | Free type fish oil | 13.5 | Glycerol 0.10 | Sodium methoxide solution 0.010 | 100 | 1 | 13.3 | 94.6 | 98.5 |
| 4 | Methyl ester type fish oil | 27.1 | Glyceryl triacetate 0.15 | Sodium ethoxide 0.025 | 80 | 3 | 26.8 | 95.7 | 97.5 |
| 5 | Free type algae oil | 53.6 | Triformin 0.20 | Sodium ethoxide solution 0.050 | 140 | 2 | 53.1 | 94.9 | 97.9 |
| 6 | Ethyl ester type algae oil | 68.5 | Glycerol 0.05 | Sodium methoxide 0.001 | 100 | 4 | 68.2 | 94.7 | 97.5 |
| 7 | Free type linoleic acid | 42.1 | Glycerol 0.10 | Potassium ethoxide 0.010 | 100 | 6 | 41.9 | 95.3 | 98.1 |
| 8 | Methyl ester type linoleic acid | 36.7 | Tributyrin 1.00 | Sodium isopropoxide 0.050 | 120 | 4 | 36.2 | 96.1 | 97.5 |
| 9 | Ethyl ester type linoleic acid | 78.3 | Glycerol 0.30 | Potassium methoxide solution 0.020 | 180 | 7 | 78.1 | 95.8 | 98.5 |
| 10 | Free type conjugated | 92.4 | Glycerol 0.15 | Sodium isobutoxide solution 0.100 | 130 | 8 | 92.0 | 94.8 | 97.9 |
| 11 | Ethyl ester type conjugated linoleic acid | 46.7 | Glyceryl triacetate 0.40 | Sodium tert-butoxide 0.03 | 100 | 3 | 46.2 | 96.0 | 98.1 |
| 12 | Free type linolenic acid | 46.9 | Glyceryl triacetate 0.15 | Sodium tert-butoxide solution 0.10 | 80 | 6 | 46.3 | 95.2 | 97.5 |
| 13 | Ethyl ester type linolenic acid | 68.2 | Tripropionin 0.60 | Sodium tert-amylate solution 0.10 | 140 | 10 | 68.0 | 95.1 | 98.5 |
| 14 | Free type arachidonic acid | 53.2 | Glycerol 0.65 | Potassium tert-butoxide 0.02 | 100 | 3 | 52.8 | 96.1 | 97.9 |
| 15 | Ethyl ester type arachidonic acid | 98.1 | Glycerol triacetate 0.50 | Potassium tert-butoxide 0.10 | 200 | 6 | 97.9 | 94.9 | 97.9 |

Note:
the "Glycerol or Glyceride (g/g)" is referred to as the weight ratio of Glycerol or Glyceride (g) to Polyunsaturated fatty acid material (g);
"Catalyst (g/g)" is referred to as the weight ratio of Catalyst (g) to Polyunsaturated fatty acid material (g);
"Relative content of triglyceride polyunsaturated fatty acid (%)" is referred to as the ratio (%) of triglyceride polyunsaturated fatty acid to Total content of polyunsaturated fatty acid.

It can be seen from Examples 3~15 of the present invention that the process has such advantages as less catalyst, simple and easily obtained catalyst, low cost, simple equipment and simple process. The process is basically carried out by one step reaction by direct conversion of the polyunsaturated fatty acid material to glyceride type polyunsaturated fatty acid. And the final product has better quality, high yield with more than 97.5%. The process of the present invention has good safety and environmental protection and is suitable for large-scale industrial production.

Although the present invention has been described in connection with the above embodiments, it should be understood that the present invention is not limited to such preferred embodiments and procedures set forth above. The embodiments and procedures were chosen and described in order to best explain the principles of the invention and its practical application, to thereby enable others skilled in the art to best utilize the invention. It will be apparent to those skilled in the art that various substitution, modifications and changes may be thereto without departing from the scope and spirit of the invention. Therefore, the intention is intended to cover all alternative constructions and equivalents falling within the spirit and scope of the invention as defined only by the appended claims and equivalents thereto.

The invention claimed is:

1. A method of preparing a glyceride type polyunsaturated fatty acid, comprising:
   1) feeding: firstly mixing a basic catalyst with glycerol or glyceride uniformly to form a mixture, then adding the mixture to a polyunsaturated fatty acid material slowly under stirring; wherein the basic catalyst comprises one or more of sodium alcoholate with formula $R_1$—ONa, a solution of sodium alcoholate with formula $R_1$—ONa, potassium alcoholate with formula $R_2$—OK, and a solution of potassium alcoholate with formula $R_2$—OK, where $R_1$ and $R_2$ represent same or different $C_1$~$C_5$ alkyl group; the polyunsaturated fatty acid material is selected from the group consisting of free type polyunsaturated fatty acid, methyl ester type polyunsaturated fatty acid and ethyl ester type polyunsaturated fatty acid;
   2) reaction: heating to 80~200° C. of temperature after completion of feeding, and then recovering low boiling point substances produced by the reaction by condensating; and
   3) washing and recycling product: cooling the reaction vessel to 0~60° C. after completion of the reaction, adding a small amount of water to extract the basic catalyst, and recovering a small amount of remaining water in an organic layer, to obtain a glyceride type polyunsaturated fatty acid product.

2. The method according to claim 1, wherein the glyceride type polyunsaturated fatty acid is selected from the group consisting of triglyceride polyunsaturated fatty acid, diglyceride polyunsaturated fatty acid, and monoglyceride polyunsaturated fatty acid.

3. The method according to claim 1, wherein the polyunsaturated fatty acid material is selected from the group consisting of fish oil, algae oil, linoleic acids, conjugated linoleic acids, linolenic acids, and arachidonic acids.

4. The method according to claim 1, wherein the content of the polyunsaturated fatty acid of the polyunsaturated fatty acid material is 10~100 wt %.

5. The method according to claim 1, wherein the glyceride comprises a glyceride with a formula

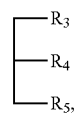

wherein $R_3$, $R_4$, $R_5$ represent hydroxyl group or $C_1\sim C_4$ lower carboxylic acid group, $R_3$, $R_4$, $R_5$ are same or different, but $R_3$, $R_4$, $R_5$ cannot be simultaneously a hydroxyl group.

6. The method according to claim 5, wherein, $R_3$, $R_4$, $R_5$ are formic acid group, acetic acid group, propionic acid group, n-butyric acid group, or isobutyric acid group.

7. The method according to claim 1, wherein, the $C_1\sim C_5$ lower alkyl group is methyl, ethyl, propyl, isopropyl, butyl, isobutyl, tert-butyl, pentyl, isopentyl, or tert-pentyl.

8. The method according to claim 1, wherein the weight ratio of feeding amount of the polyunsaturated fatty acid material, the glycerol or the glyceride, and the basic catalyst is 100:1~100:0.1~10.

9. The method according to claim 1, wherein the time of the esterification reaction is 1~10 hours.

* * * * *